United States Patent
Suzuki et al.

(10) Patent No.: US 11,638,571 B2
(45) Date of Patent: May 2, 2023

(54) ULTRASOUND PROBE AND ULTRASOUND DIAGNOSTIC APPARATUS

(71) Applicant: Konica Minolta, Inc., Tokyo (JP)

(72) Inventors: Kenji Suzuki, Tokyo (JP); Yuta Nakayama, Chiba (JP)

(73) Assignee: KONICA MINOLTA, INC., Tokyo (JP)

( * ) Notice: Subject to any disclaimer, the term of this patent is extended or adjusted under 35 U.S.C. 154(b) by 682 days.

(21) Appl. No.: 16/358,303

(22) Filed: Mar. 19, 2019

(65) Prior Publication Data
US 2019/0290242 A1    Sep. 26, 2019

(30) Foreign Application Priority Data
Mar. 26, 2018    (JP) .............................. JP2018-058104

(51) Int. Cl.
| | | |
|---|---|---|
| *A61B 8/00* | (2006.01) | |
| *B06B 1/06* | (2006.01) | |
| *H01L 41/187* | (2006.01) | |
| *H01L 41/193* | (2006.01) | |

(52) U.S. Cl.
CPC ............ *A61B 8/4488* (2013.01); *A61B 8/461* (2013.01); *B06B 1/064* (2013.01); *B06B 1/0607* (2013.01); *B06B 2201/76* (2013.01); *H01L 41/1876* (2013.01); *H01L 41/193* (2013.01)

(58) Field of Classification Search
None
See application file for complete search history.

(56) References Cited

U.S. PATENT DOCUMENTS

| | | | |
|---|---|---|---|
| 2009/0182237 A1 | 7/2009 | Angelsen et al. | |
| 2009/0204001 A1* | 8/2009 | Ona ...................... | B06B 1/0622 600/443 |
| 2010/0327695 A1 | 12/2010 | Goel et al. | |
| 2011/0062535 A1* | 3/2011 | McMullen ............ | B06B 1/0292 257/419 |

(Continued)

FOREIGN PATENT DOCUMENTS

| | | |
|---|---|---|
| EP | 2666547 A2 | 11/2013 |
| JP | 2009296055 A | 12/2009 |

(Continued)

OTHER PUBLICATIONS

JPO, Office Action for the corresponding Japanese Patent Application No. 2018-058104, dated Jul. 6, 2021, with English translation.

(Continued)

*Primary Examiner* — Katherine L Fernandez
(74) *Attorney, Agent, or Firm* — Lucas & Mercanti, LLP (57) ABSTRACT

An ultrasound probe and ultrasound diagnostic apparatus that achieve high transmission/reception sensitivity and wide frequency band are provided. The ultrasound probe includes a pMUT array in which a plurality of pMUTs are arranged. The pMUTs include first pMUTs for ultrasound transmission and pMUTs for ultrasound wave reception having a structure different from that of the first pMUTs. The cell region of each first pMUT and the cell region of each second pMUT are separated from each other in the ultrasound wave radiation plane.

15 Claims, 6 Drawing Sheets

(56) References Cited

U.S. PATENT DOCUMENTS

| | | | |
|---|---|---|---|
| 2011/0213251 A1* | 9/2011 | Robinson | G01S 7/5208 |
| | | | 600/459 |
| 2011/0291207 A1* | 12/2011 | Martin | G10K 9/125 |
| | | | 257/E21.53 |
| 2015/0244473 A1* | 8/2015 | Saulnier | H04R 17/00 |
| | | | 367/134 |
| 2016/0045184 A1* | 2/2016 | Courtney | A61B 8/483 |
| | | | 600/424 |
| 2016/0107194 A1* | 4/2016 | Panchawagh | G01S 7/5208 |
| | | | 367/140 |
| 2017/0172618 A1* | 6/2017 | Erkamp | A61B 17/3417 |
| 2018/0242849 A1* | 8/2018 | Fukutani | G01N 29/2418 |
| 2019/0076114 A1* | 3/2019 | Sammoura | A61N 1/3787 |
| 2020/0338592 A1* | 10/2020 | Goericke | B06B 1/0685 |

FOREIGN PATENT DOCUMENTS

| | | |
|---|---|---|
| JP | 2011-109448 A | 6/2011 |
| JP | 2015-517752 A | 6/2015 |
| WO | 2019055178 A1 | 3/2019 |

OTHER PUBLICATIONS

Robert A Dorey et al, "Fabrication and Characterization of Annual Thickness Mode Piezoelectric Micro Ultrasonic Transducers," IEEE Transactions on Ultrasonics, Ferroelectrics and Frequency Control, IEEE, Dec. 1, 2007, pp. 2462-2468, vol. 54, No. 12, US.

EPO, Extended European Search Report for the corresponding European Patent Application No. 19163841.0, dated Aug. 19, 2019 (11 pages).

* cited by examiner

ULTRASOUND PROBE AND ULTRASOUND DIAGNOSTIC APPARATUS

CROSS REFERENCE TO RELATED APPLICATIONS

The entire disclosure of Japanese Patent Application No. 2018-058104 filed on Mar. 26, 2018 is incorporated herein by reference in its entirety.

BACKGROUND

Technological Field

The present invention relates to an ultrasound probe and an ultrasound diagnostic apparatus for ultrasound diagnosis.

Description of Related Art

Conventionally, an ultrasound probe having an ultrasound wave radiation surface in which a plurality of ultrasound transducers are arranged is known. In recent years, as an ultrasound transducer, an ultrasound probe employing a piezoelectric element produced by micro electro mechanical systems (MEMS) (so-called piezoelectric micromachined ultrasound transducer (pMUT)) has been increasingly developed (see, e.g. Japanese Unexamined Patent Application Publication (Translation of PCT Application) No. 2015-517752 (PTL 1)).

The ultrasound probe employing the pMUT can transmit and receive ultrasound waves by vibrating (deflection vibration) a diaphragm including a piezoelectric body like a drum, for example. The pMUT can be finely produced in comparison with a piezoelectric element obtained by dividing a bulk PZT (lead zirconate titanate) by dicing or the like. Therefore, the pMUT can achieve higher frequency and higher resolution and is suitable for two-dimensional array of the piezoelectric element for generating three-dimensional images, and, can reduce the size and thickness. However, in the case where the same deflection vibration is used for transmission and reception as in conventional pMUTs, the frequency range is narrowed and the usable frequency is limited to the range around the resonance frequency.

PTL 1 discloses a pMUT array in which a plurality of pMUTs having different resonance frequencies are arranged to achieve wider band (see FIG. 7B).

In an ultrasound probe including the pMUT array disclosed in PTL 1, however, a deep alley (dead band) might be formed between resonance peaks, thus deteriorating the quality of ultrasound images. In addition, since a plurality of resonance frequencies are mixed, the transmission/reception sensitivity of the ultrasound probe might be reduced as a whole.

SUMMARY

An object of the present invention is to provide an ultrasound probe and an ultrasound diagnostic apparatus that achieve high transmission/reception sensitivity and wide frequency band.

An ultrasound probe reflecting an aspect of the present invention includes a pMUT array in which a plurality of pMUTs are arranged. The plurality of pMUTs include a plurality of first pMUTs for ultrasound transmission, and a plurality of second pMUTs for ultrasound wave reception, each second pMUT having a structure different from that of each first pMUT; and a cell region of each first pMUT and a cell region of each second pMUT are separated from each other in an ultrasound wave radiation plane.

An ultrasound diagnostic apparatus reflecting an aspect of the present invention includes: the above-mentioned ultrasound probe; and an ultrasound diagnostic apparatus main body to which the ultrasound probe is connected, the ultrasound diagnostic apparatus main body being configured to generate an ultrasound image based on an ultrasound signal from the ultrasound probe.

BRIEF DESCRIPTION OF DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Hereinafter, one or more embodiments of the present invention will be described with reference to the drawings. However, the scope of the invention is not limited to the disclosed embodiments.

Embodiments of the present invention are elaborated below with reference to the accompanying drawings.

First Embodiment

Figure 1:
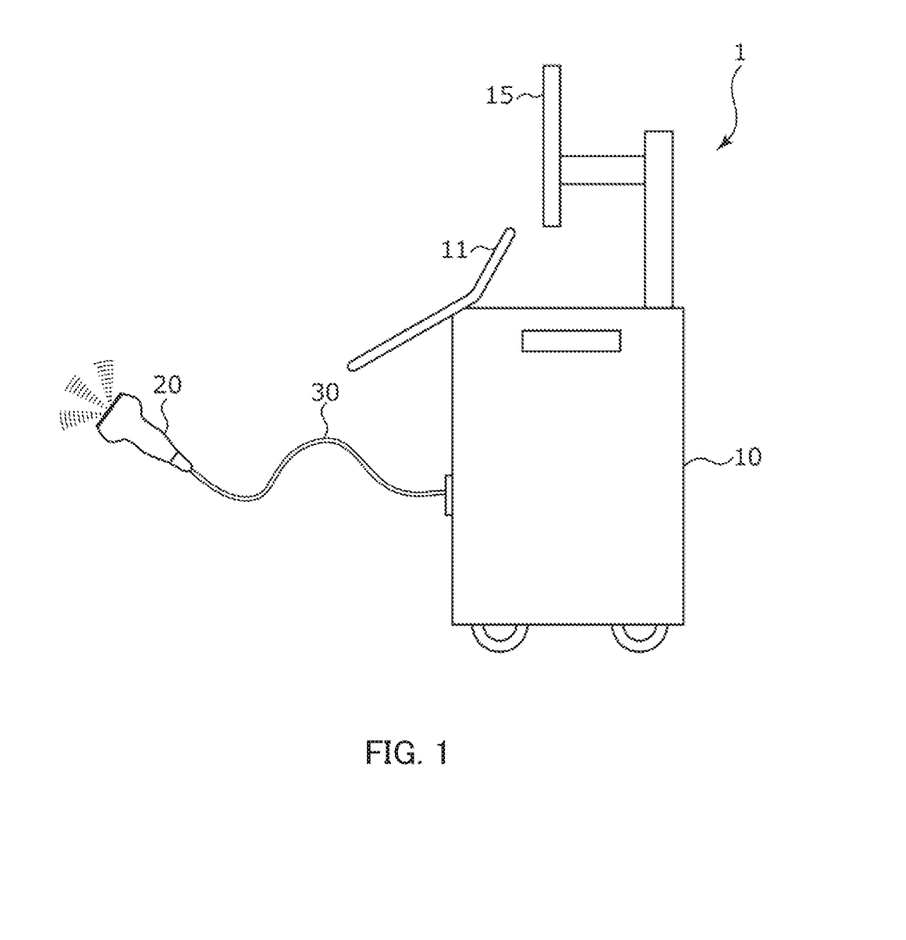
FIG. 1 illustrates an external appearance of an ultrasound diagnostic apparatus according to an embodiment.
Figure 2:
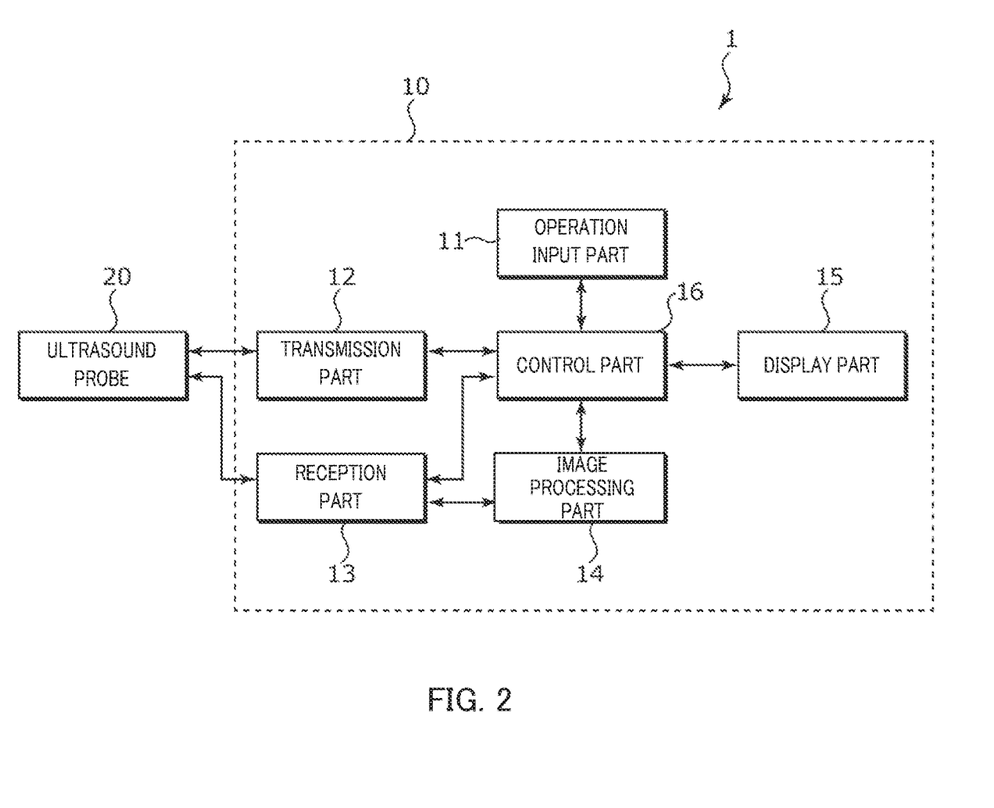
FIG. 2 is a block diagram illustrating a principal part of a control system of the ultrasound diagnostic apparatus.

FIG. 1 illustrates an external appearance of ultrasound diagnostic apparatus 1 according to an embodiment of the present invention. FIG. 2 is a block diagram illustrating a principal part of a control system of ultrasound diagnostic apparatus 1.

As illustrated in FIG. 1, ultrasound diagnostic apparatus 1 includes ultrasound diagnostic apparatus main body 10 and ultrasound probe 20. Ultrasound diagnostic apparatus main body 10 and ultrasound probe 20 are connected with each other through cable 30.

Ultrasound diagnostic apparatus 1 is used for image diagnosis by visualizing the shapes, properties and/or movements in a subject in the form of an ultrasound image. Note that ultrasound diagnostic apparatus 1 may generate any ultrasound image, such as B-mode images, color Doppler images, three-dimensional ultrasound images, and M-mode images. Likewise, ultrasound probe 20 may be any probe, such as convex probes, linear probes, sector probes, and three-dimensional probes.

Ultrasound probe 20 transmits ultrasound waves to a subject, and receives ultrasound waves (echoes) reflected by the subject. Ultrasound probe 20 converts the received signal and transmits the signal to diagnosis apparatus main body 10. Details of ultrasound probe 20 are described later.

Using a reception signal from ultrasound probe 20, ultrasound diagnostic apparatus main body 10 visualizes the internal state of the subject in the form of an ultrasound image. Specifically, as illustrated in FIG. 2, ultrasound diagnostic apparatus main body 10 includes operation input part 11, transmission part 12, reception part 13, image processing part 14, display part 15 and the like.

Operation input part 11 receives an input of a command of the start of a diagnosis and the like or information relating to a subject, for example. Operation input part 11 includes an operation panel having a plurality of input switches, a keyboard, a mouse and the like, for example.

In accordance with an instruction of control part 16, transmission part 12 generates a transmission signal (driving signal) and transmits the signal to ultrasound probe 20.

Reception part 13 receives a reception signal from ultrasound probe 20, and outputs the signal to image processing part 14.

In accordance with an instruction of control part 16, image processing part 14 generates an ultrasound image (e.g. a B-mode image, a color Doppler image, and a three-dimensional ultrasound image) representing the internal state of the subject by performing a predetermined signal process (e.g. a logarithmic compression process, a detection process, an FFT analysis process and the like) on a reception signal from reception part 13. Note that the process for generating an ultrasound image is publicly known, and therefore the description thereof is omitted here.

Display part 15 is composed of a liquid crystal display or the like, and displays an ultrasound image generated in image processing part 14, for example.

Control part 16 controls the entirety of ultrasound diagnostic apparatus 1 by controlling operation input part 11, transmission part 12, reception part 13, image processing part 14 and display part 15, in accordance with their functions.

Figure 3:
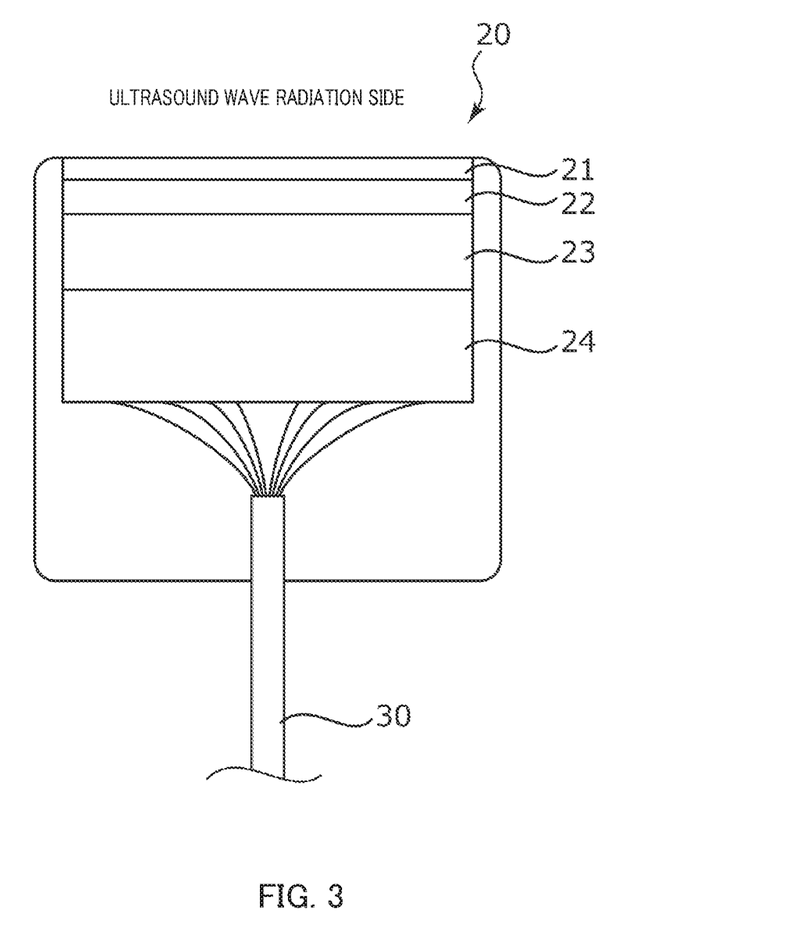
FIG. 3 illustrates a configuration of an ultrasound probe.

FIG. 3 illustrates a configuration of ultrasound probe 20. As illustrated in FIG. 3, ultrasound probe 20 includes protective layer 21, pMUT array 22, signal processing circuit 23 and bucking material 24 in this order from the ultrasound wave radiation side. Protective layer 21 may include an acoustic lens and an alignment layer.

Protective layer 21 protects the surface (ultrasound wave radiation surface) of pMUT array 22. The material (e.g. silicone rubber or the like) of protective layer 21 is a material that is close to an acoustic impedance of human bodies and does not cause discomfort when touching a human body.

Signal processing circuit 23 is a circuit that generates a transmission signal for ultrasound transmission and/or performs processing on a reception signal (ultrasound signal). In the present embodiment, signal processing circuit 23 is connected with ultrasound diagnostic apparatus main body 10 through cable 30. Alternatively, signal processing circuit 23 may have a radio communication function of connection with ultrasound diagnostic apparatus main body 10 for information communications without using cable 30.

Bucking material 24 attenuates unnecessary vibrations generated at pMUT array 22.

Figure 4A:
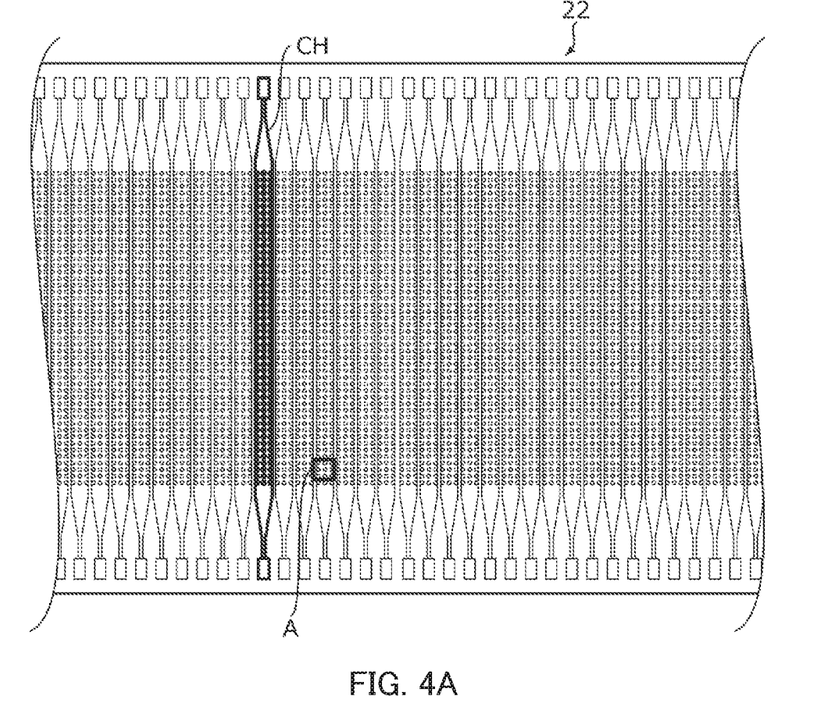
FIG. 4A and FIG. 4B are plan views illustrating an arrangement of pMUTs.
Figure 4B:
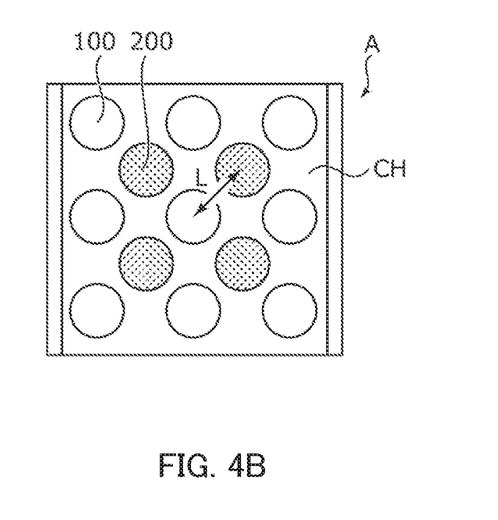

As illustrated in FIG. 4A and FIG. 4B, pMUT array 22 includes a plurality of pMUTs 100 and 200 that are two-dimensionally arranged. FIG. 4A is a plan view illustrating an arrangement of pMUTs 100 and 200 in pMUT array 22, and FIG. 4B is an enlarged view of region A indicated with the heavy line in FIG. 4A. The pMUTs 100 and 200 are divided into a plurality of channels CH in the scan direction, and are driven for each channel CH.

In the present embodiment, pMUT 100 is a first pMUT (hereinafter referred to as "first pMUT 100") for ultrasound transmission, and pMUT 200 is a second pMUT (hereinafter referred to as "second pMUT 200") for ultrasound wave reception. First pMUT 100 and second pMUT 200 have different structures. In addition, first pMUT 100 and second pMUT 200 are formed such that their cell regions are separated from each other (do not overlap each other) in the ultrasound wave radiation plane. In the relationship with pMUT array 22, each of pMUTs 100 and 200 of pMUT array 22 is referred to as "pMUT cell".

In the present embodiment, first pMUTs 100 and second pMUTs 200 are disposed in a lattice form. By using a MEMS technique, first pMUTs 100 and second pMUTs 200 having different structures can be separately formed.

Figure 5:
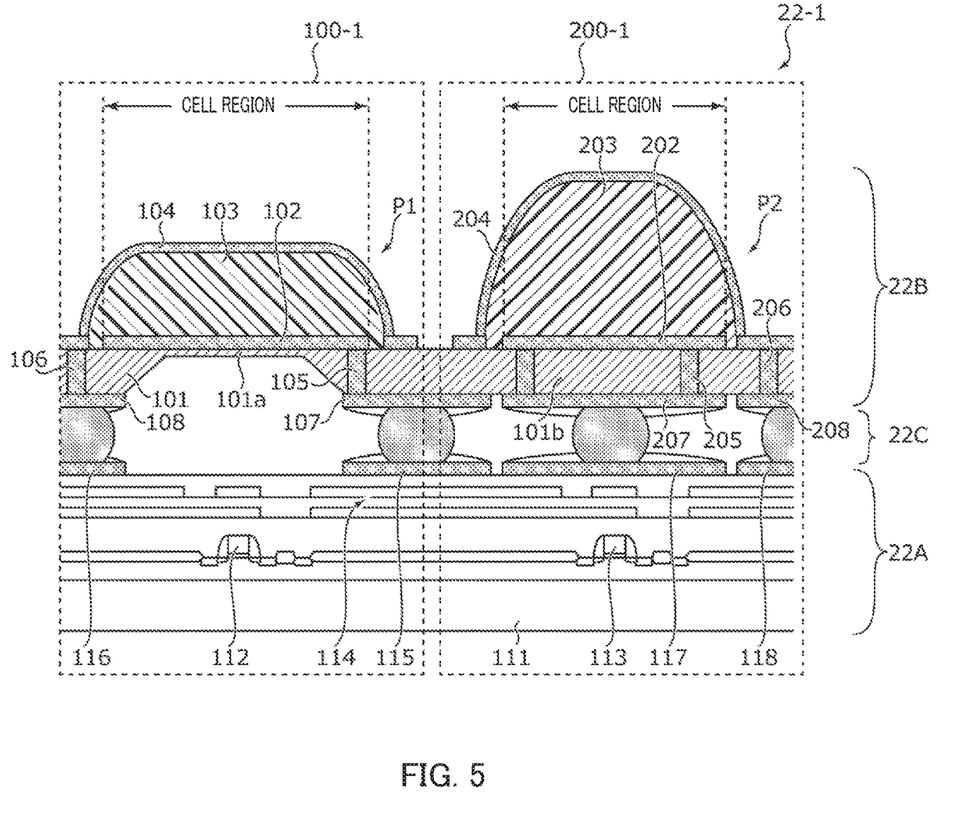
FIG. 5 is a sectional view illustrating a configuration of a pMUT array according to a first embodiment.

The cell region is an effective region where ultrasound waves are transmitted or received, and is a region where all elements of a lamination structure including a piezoelectric body and two electrodes sandwiching the piezoelectric body overlap each other (see FIG. 5). That is, the cell region is defined by the size of one of the piezoelectric body and the electrode, which has the smaller planar shape than the other. FIG. 4B indicates that the cell regions of first pMUTs 100 and second pMUTs 200 do not overlap each other in the ultrasound wave radiation plane.

Preferably, in pMUT array 22, the center-to-center distance L of the cells of first pMUT 100 and second pMUT 200 adjacent to each other satisfies $L \leq \lambda c/2$ where $\lambda c$ represents a wavelength in a living body (representative sound velocity: 1530 m/sec) with respect to center frequency F of the ultrasound wave frequency band used in ultrasound diagnostic apparatus 1. With this configuration, first pMUT 100 and second pMUT can be regarded as the same sound source, and the paths of the transmission ultrasound beam and the reception ultrasound beam can match.

Note that the arrangement of first pMUT 100 and second pMUT 200 is not limited to the arrangement illustrated in FIG. 4A and FIG. 4B. First pMUT 100 and second pMUT 200 may be disposed in a triangular lattice form or a hexagram form, or, may be disposed at random, for example.

In addition, the numbers of the cells of first pMUTs 100 and second pMUTs in a channel may be different from each other. For example, in the case where the transmission sound pressure intensity can be ensured with a small number of cells in a low frequency region, it is preferable to reduce the number of first pMUTs 100 and increase the number of second pMUTs 200.

FIG. 5 is a sectional view illustrating a configuration of pMUT array 22 according to the first embodiment. In the following description, ultrasound probe 20 according to the first embodiment is referred to as "ultrasound probe 20-1", pMUT array 22 is referred to as "pMUT array 22-1", first pMUT 100 is referred to as "first pMUT 100-1", and second pMUT 200 is referred to as "second pMUT 200-1".

As illustrated in FIG. 5, pMUT array 22-1 according to the first embodiment includes electronic circuit substrate 22A, piezoelectric element substrate 22B, and connecting part 22C.

Electronic circuit substrate 22A performs a driving control and a reception control of piezoelectric element parts P1 and P2 of first pMUT 100-1 and second pMUT 200-1. Electronic circuit substrate 22A is a CMOS substrate in which transmitting circuit 112, receiving circuit 113 and wiring layer 114 are formed on substrate 111, for example.

Transmitting circuit 112 controls the driving of first pMUT 100-1. Receiving circuit 113 detects a signal from second pMUT 200. Wiring layer 114 electrically connects between transmitting circuit 112 and receiving circuit 113, and piezoelectric element parts P1 and P2.

Piezoelectric element substrate 22B includes first piezoelectric element part P1, second piezoelectric element part P2 and substrate 101.

First piezoelectric element part P1 includes first lower electrode 102, first piezoelectric body 103, and first upper electrode 104 that are sequentially stacked on substrate 101. First piezoelectric element part P1 has a unimorph structure in which first piezoelectric body 103 is sandwiched between lower electrode 102 and upper electrode 104.

Through the through electrode 105 provided in substrate 101, lower electrode 102 is drawn to connection electrode (bump) 107 provided in the rear surface of substrate 101. Connection electrode 107 is electrically connected with transmitting circuit 112 through connecting part 22C and wiring layer 114 of electronic circuit substrate 22A.

Through the through electrode 106 provided in substrate 101, upper electrode 104 is drawn to connection electrode 108 provided in the rear surface of substrate 101. Connection electrode 108 is connected with common electrode (GND) 116 through connecting part 22C and wiring layer 114 of electronic circuit substrate 22A.

Lower electrode 102, upper electrode 104 and connection electrodes 107 and 108 are formed of a conductive oxide or a metal material such as Pt, Au and Ti. For example, through electrodes 105 and 106 may be formed of a metal material such as Cu, W and Al, or may be formed by doping impurities such as B (boron) in substrate 101 so as to provide conductivity.

First piezoelectric body 103 is formed of a piezoelectric material that provides excellent ultrasound transmission performance (transmission sensitivity and frequency band). It is desirable that first piezoelectric body 103 be formed of a material that has a large inverse piezoelectric constant and is thus largely deformed by voltage application. In the present embodiment, first piezoelectric body 103 is formed of PZT.

Note that first piezoelectric body 103 may be formed of an inorganic piezoelectric material other than PZT (e.g. PMN-PT (lead titanate magnesiumniobate), PMN-PZT (magnesium niobic acid zircon lead titanate) or the like).

Second piezoelectric element part P2 includes second lower electrode 202, second piezoelectric body 203 and second upper electrode 204 that are sequentially stacked on substrate 101. As with first piezoelectric element part P2, second piezoelectric element part P2 has a unimorph structure in which second piezoelectric body 203 is sandwiched between lower electrode 202 and upper electrode 204.

Through the through electrode 205 provided in substrate 101, lower electrode 202 is drawn to connection electrode 207 provided in the rear surface of substrate 101. Connection electrode 207 is electrically connected with receiving circuit 113 through connecting part 22C and wiring layer 114 of electronic circuit substrate 22A.

Through the through electrode 206 provided in substrate 101, upper electrode 204 is drawn to connection electrode 208 provided in the rear surface of substrate 101. Connection electrode 208 is connected with common electrode (GND) 118 through connecting part 22C and wiring layer 114 of electronic circuit substrate 22A.

Lower electrode 202, upper electrode 204 and connection electrodes 207 and 208 are formed of a conductive oxide or a metal material such as Pt, Au, and TI, for example. Through electrodes 205 and 206 are formed of a metal material such as Cu, W, and Al, or may be formed by doping impurities in substrate 101, for example.

Second piezoelectric body 203 is formed of a piezoelectric material that provides excellent ultrasound reception performance (reception sensitivity and frequency band). Second piezoelectric body 203 generates a voltage when receiving ultrasound waves. In the present embodiment, second piezoelectric body 203 is formed of a polyvinylidene fluoride (PVDF) resin. Although PVDF is inferior to PZT in ultrasound transmission performance, PVDF has a small dielectric constant and therefore provides remarkably high voltage reception performance. For example, the voltage reception sensitivity of a pMUT employing PVDF is ten times that of a pMUT employing PZT.

Preferably, thickness t of second piezoelectric body 203 is ¼ or smaller of wavelength $\lambda_p$ in piezoelectric body 203 with respect to the maximum frequency $F_{max}$ of the ultrasound wave frequency band used in ultrasound diagnostic apparatus 1. When $t \leq \lambda_p/4$ is met, resonance in the thickness direction can be prevented and a wide band width can be ensured since one surface of second piezoelectric body 203 is the fixed end.

When the center frequency of the ultrasound wave frequency band used in ultrasound diagnostic apparatus 1 is represented by $F_c$, maximum frequency $F_{max}=2F_c$, and therefore the condition that second piezoelectric body 203 does not resonate in the band is $t \leq \lambda_p/4 = V/4F_{max} = V/8F_c$. Typically, center frequency $F_c$ of the ultrasound waves used in ultrasound diagnostic apparatus 1 for medical use is about 20 MHz at maximum, and therefore, when the sound velocity V in PVDF is set to 2560 m/sec, $t \leq 2560/(8 \times 20) = 16$ [μm]. That is, when the thickness of second piezoelectric body 203 is set to 16 μm or smaller in ultrasound probe 20-1, resonance in the thickness direction can be prevented.

Note that second piezoelectric body 203 may be formed of an organic piezoelectric material other than PVDF (e.g. urea resin). In addition, second piezoelectric body 203 may have a single layer structure composed only of a piezoelectric material. Alternatively, in the case where thickening is performed by applying a piezoelectric material multiple times, second piezoelectric body 203 may have a lamination structure in which a metal or non-metal thin film layer is sandwiched by the piezoelectric material.

Substrate 101 is an Si substrate, for example. Substrate 101 includes thin film part 101a in a portion corresponding to first piezoelectric element part P1. Thin film part 101a is formed by etching the region corresponding to first piezoelectric element part P1 in a recessed shape on the rear side (the side opposite to the side on which first piezoelectric element part P1 is formed) of substrate 101. On the other hand, the portion corresponding to second piezoelectric element part P2 of substrate 101 is not etched, and is thicker than thin film part 101a (thick film part 101b).

That is, first pMUT 100-1 has a diaphragm structure composed of first piezoelectric element part P1 and thin film part 101a. With voltage application, first pMUT 100-1 vibrates in a deflection vibration mode, and emits ultrasound waves. Here, the diaphragm is a structure that induces, within the frequency band (the band width of −40 dB) of the transmission/reception sensitivity, the deflection mode resonance of the vibration plate whose end portion is held. Deflection of the vibration plate is displacement of the vibration plate in the vertical direction (thickness direction) that is caused by expansion and contraction of the piezoelectric body (here, first pMUT 100-1) in the longitudinal direction of the vibration plate (here, thin film part 101a).

Preferably, first pMUT 100-1 has one or more resonance points in the frequency band. With such a configuration, a large transmission sensitivity can be obtained at or near the resonance point. Further, since the transmission sensitivity property is the ultrasound wave intensity (sound pressure level) and is proportional to the product of the transducer displacement and the frequency, the transmission sensitivity property does not sharply attenuate on the high frequency side of the resonance frequency, and thus the band width can be widened even with the resonance point.

Note that the diaphragm structure of first pMUT 100-1 is designed such that the effective acoustic impedance matches the acoustic impedance of a living body. With such a configuration, ultrasound waves can efficiently propagate inside of a living body. Specifically, it suffices that the rigidity of the diaphragm structure is optimized. More preferably, in accordance with the resonance frequency, the transmission performance (transmission sensitivity, frequency band) and the like, the material of substrate 101, the thickness of thin film part 101a, the thickness of first piezoelectric body 103, the cell region of first pMUT 100-1 and the like are appropriately optimized.

Second pMUT 200-1 has a non-diaphragm structure composed of second piezoelectric element part P2 and thick film part 101b. Second pMUT 200-1 generates a voltage when receiving ultrasound waves and deforming in the thickness direction.

Since second pMUT 200-1 has a non-diaphragm structure and formation of a recess in substrate 101 is unnecessary, second pMUT 200-1 can be formed in the same radiation plane without reducing the density of first pMUT 100-1.

Preferably, second pMUT 200-1 does not have the resonance point in the frequency band. With such a configuration, wide reception band width can be obtained. One reason for this is that, when there is a resonance point, abrupt attenuation occurs on the higher frequency side of the resonance frequency, resulting in a narrowband since the reception sensitivity property is the voltage signal and is proportional to the displacement of the transducer.

While second pMUT 200-1 need not have a diaphragm structure since the PVDF that is the organic piezoelectric film is close to the living body acoustic impedance, thick film part 101b may be slightly etched as long as no deflection mode resonance is present in the frequency band.

Connecting part 22C is interposed between electronic circuit substrate 22A and piezoelectric element substrate 22B so as to physically and electrically connect electronic circuit substrate 22A and piezoelectric element substrate 22B. With this configuration, electronic circuit substrate 22A and piezoelectric element substrate 22B can be appropriately manufactured by respective manufacturing methods.

Preferably, connecting part 22C is formed with an anisotropic conductive film (ACF), for example. Specifically, by sandwiching an ACF composed of a film-shaped insulation resin material in which minute conductive particles are dispersed between electronic circuit substrate 22A and piezoelectric element substrate 22B and by applying heat and pressure thereto, the substrates can be bonded together. With this configuration, the connection electrodes (bumps) of electronic circuit substrate 22A and piezoelectric element substrate 22B can be brought into conduction through the conductive particles, and the conduction portions can be more surely insulated with the insulation resin material. In addition, it is possible to suppress reduction in performance that is caused when electronic circuit substrate 22A and piezoelectric element substrate 22B are bonded to each other.

Note that electronic circuit substrate 22A and piezoelectric element substrate 22B may be joined together by other methods. For example, it is possible to employ bonding using a conductive adhesive agent and metal-coated spherical glass, diffusion bonding (thermo-compression bonding), eutectic bonding, or welding.

As described above, ultrasound probe 20-1 according to the first embodiment is an ultrasound probe including pMUT array 22-1 in which a plurality of pMUTs 100-1 and 200-1 are arranged, and pMUTs 100-1 and 200-1 include first pMUT 100-1 for ultrasound transmission and second pMUT 200-1 for ultrasound wave reception having a structure differing from that of first pMUT 100-1. The cell regions of first pMUT 100-1 and second pMUT 200-1 are separated in the ultrasound wave radiation plane.

In addition, first pMUT 100-1 has a configuration in which first lower electrode 102, first piezoelectric body 103 and first upper electrode 104 are sequentially stacked on substrate 101, and second pMUT 200-1 has a configuration in which second lower electrode 202, second piezoelectric body 203 and second upper electrode 204 are sequentially stacked on substrate 101. First piezoelectric body 103 and second piezoelectric body 203 are formed of different materials.

Specifically, first piezoelectric body 103 is formed of an inorganic piezoelectric material (e.g. PZT) suitable for ultrasound transmission, and second piezoelectric body 203 is formed of an organic piezoelectric material (e.g. PVDF) suitable for ultrasound wave reception.

Since first pMUT 100-1 for ultrasound transmission and second pMUT 200-1 for ultrasound wave reception are separately arranged in the ultrasound wave radiation surface by means of MEMS in ultrasound probe 20-1, an ultrasound probe having high transmission/reception sensitivity and wide frequency band can be achieved. In addition, with ultrasound diagnostic apparatus 1 provided with ultrasound probe 20-1, a high-quality ultrasound image can be obtained.

Second Embodiment

Figure 6:
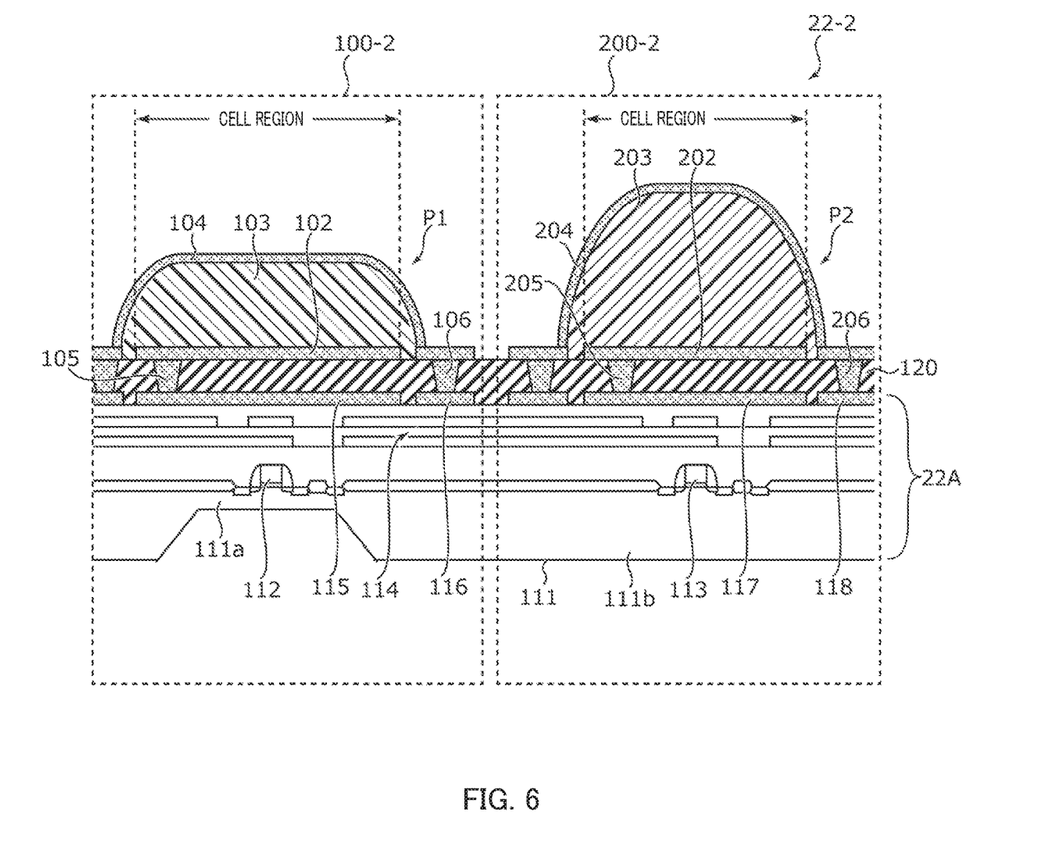
FIG. 6 is a sectional view illustrating a configuration of a pMUT array according to a second embodiment.

FIG. 6 is a sectional view illustrating a configuration of pMUT array 22 according to a second embodiment. In the following description, ultrasound probe 20 according to the second embodiment is referred to as "ultrasound probe 20-2", pMUT array 22 is referred to as "pMUT array 22-2", first pMUT 100 is referred to as "first pMUT 100-2", and second pMUT 200 is referred to as "second pMUT 200-2". In addition, the components having functions substantially identical to those of the first embodiment are denoted with the same reference numerals, and the description thereof is omitted.

As illustrated in FIG. 6, pMUT array 22-2 according to the second embodiment includes electronic circuit substrate 22A, and first piezoelectric element part P1 and second piezoelectric element part P2 are formed on electronic circuit substrate 22A with insulation layer 120 therebetween.

Electronic circuit substrate 22A performs the control and the reception control of piezoelectric element parts P1 and P2 of first pMUT 100-2 and second pMUT 200-2. Electronic circuit substrate 22A is a CMOS substrate in which transmitting circuit 112, receiving circuit 113 and wiring layer 114 are formed on substrate 111, for example.

First piezoelectric element part P1 includes first lower electrode 102, first piezoelectric body 103 and first upper electrode 104 sequentially stacked on insulation layer 120. First piezoelectric element part P1 has a unimorph structure in which first piezoelectric body 103 is sandwiched between lower electrode 102 and upper electrode 104.

Lower electrode 102 is electrically connected with connection electrode 115 of electronic circuit substrate 22A through the through electrode 105 provided in insulation layer 120, and is electrically connected with transmitting circuit 112 through wiring layer 114.

Upper electrode 104 is connected with common electrode (GND) 116 of electronic circuit substrate 22A through the through electrode 106 provided in insulation layer 120.

Second piezoelectric element part P2 includes second lower electrode 202, second piezoelectric body 203 and second upper electrode 204 sequentially stacked on insulation layer substrate 120. As with first piezoelectric element part P2, second piezoelectric element part P2 has a unimorph structure in which second piezoelectric body 203 is sandwiched between lower electrode 202 and upper electrode 204.

Lower electrode 202 is electrically connected with connection electrode 117 of electronic circuit substrate 22A through the through electrode 205 provided in insulation layer 120, and is electrically connected with receiving circuit 113 through wiring layer 114.

Upper electrode 204 is connected with common electrode (GND) 118 of electronic circuit substrate 22A through the through electrode 206 provided in insulation layer 120.

Substrate 111 of electronic circuit substrate 22A is an Si substrate, for example. Substrate 111 includes thin film part 111a in a portion corresponding to first piezoelectric element part P1. Thin film part 111a is formed by etching the region corresponding to first piezoelectric element part P1 in a recessed shape on the rear surface side (the side opposite to the side on which first piezoelectric element part P1 is formed) of substrate 111. On the other hand, a portion corresponding to second piezoelectric element part P2 of substrate 111 is not etched, and is thicker than thin film part 111a (thick film part 111b).

That is, first pMUT 100-2 has a diaphragm structure composed of first piezoelectric element part P1 and thin film part 111a. With voltage application, first pMUT 100-2 vibrates in a deflection vibration mode and emits ultrasound waves. Note that, in electronic circuit substrate 22A, wiring layer 14 and the like formed on substrate 111 are significantly thinner than substrate 111. That is, the thickness of electronic circuit substrate 22A depends on substrate 111. Accordingly, first pMUT 100-2 in which thin film part 111a is formed can be regarded as a diaphragm structure.

On the other hand, second pMUT 200-2 has a non-diaphragm structure composed of second piezoelectric element part P2 and thick film part 111b. Second pMUT 200-1 generates a voltage when receiving ultrasound waves and deforming in the thickness direction.

Since second pMUT 200-2 has a non-diaphragm structure and it is not unnecessary to form a recess in substrate 101, second pMUT 200-2 can be formed in the same radiation plane without reducing the density of first pMUT 100-2.

Insulation layer 120 is formed of $SiO_2$, porous silicon or the like, for example. Insulation layer 120 may have a single layer structure or a multi-layer structure. The thickness of insulation layer 120 is 3 µm or greater, for example.

By forming first piezoelectric element part P1 and second piezoelectric element part P2 on electronic circuit substrate 22A with insulation layer 120 therebetween, the insulation property between through electrodes 105, 106, 205 and 206 can be ensured, and the parasitic capacitance of electronic circuit substrate 22A can be canceled.

The manufacturing method of pMUT array 22-2 includes a first step of forming insulation layer 120 on electronic circuit substrate 22A and a second step of forming first piezoelectric element part P1 and second piezoelectric element part P2 by means of MEMS. While, in the second step, electronic circuit substrate 22A might be degraded due to the heat of film formation of first piezoelectric element part P1 and second piezoelectric element part P2, such degradation of electronic circuit substrate 22A can be prevented since insulation layer 120 functions as a heat insulating layer.

As described above, ultrasound probe 20-2 according to the second embodiment is an ultrasound probe including pMUT array 22-2 in which a plurality of pMUTs 100-2 and 200-2 are arranged, and pMUTs 100-2 and 200-2 include first pMUT 100-2 for ultrasound transmission and second pMUT 200-2 for ultrasound wave reception having a structure differing from that of first pMUT 100-2. The cell regions of first pMUT 100-2 and second pMUT 200-2 are separated in the ultrasound wave radiation plane.

In addition, first pMUT 100-2 has a structure in which first lower electrode 102, first piezoelectric body 103 and first upper electrode 104 are sequentially stacked on electronic circuit substrate 22A, and second pMUT 200-2 has a structure in which second lower electrode 202, second piezoelectric body 203 and second upper electrode 204 are sequentially stacked on electronic circuit substrate 22A. First piezoelectric body 103 and second piezoelectric body 203 are formed on different materials.

Specifically, first piezoelectric body 103 is formed of an inorganic piezoelectric material (e.g. PZT) suitable for ultrasound transmission, and second piezoelectric body 203 is formed of an organic piezoelectric material (e.g. PVDF) suitable for ultrasound wave reception.

Since first pMUT 100-2 for ultrasound transmission and second pMUT 200-2 for ultrasound wave reception are separately arranged in the ultrasound wave radiation surface in ultrasound probe 20-2, it is possible to provide an ultrasound probe with high transmission/reception sensitivity and wide frequency band. In addition, with ultrasound diagnostic apparatus 1 provided with ultrasound probe 20-2, a high-quality ultrasound image can be obtained.

While the invention made by the present inventor has been specifically described based on the preferred embodiments, it is not intended to limit the present invention to the above-mentioned preferred embodiments but the present invention may be further modified within the scope and spirit of the invention defined by the appended claims.

For example, as long as the cell regions of first pMUT 100 and second pMUT 200 are separated in the ultrasound wave radiation plane, second piezoelectric body 203 and/or second upper electrode 204 may be extended to the upper side (ultrasound wave radiation side) of first piezoelectric element part P1. For example, first upper electrode 104 and second upper electrode 204 may be provided as common members to cover the entire surfaces of first pMUT 100 and second pMUT 200.

For example, upper electrodes 104 and 204 operate as a common electrode, mainly a GND, in acoustic transmission and reception, but preferably are separated from GND as polarizing electrodes of piezoelectric bodies 103 and 203. Before the process, they are used as polarizing electrodes in a divided state, and after the polarization process, they are electrically connected with GND so as to be used as probes. In addition, with a configuration allowing for connection and separation in a programmable manner, polarization control of a manufactured product can be achieved.

Although embodiments of the present invention have been described and illustrated in detail, the disclosed embodiments are made for purpose of illustration and example only and not limitation. The scope of the present invention should be interpreted by terms of the appended claims.

What is claimed is:

1. An ultrasound probe comprising a piezoelectric micromachined ultrasound transducer (pMUT) array in which a plurality of pMUTs are arranged, wherein:
   the plurality of pMUTs include a plurality of first pMUTs for ultrasound transmission, and a plurality of second pMUTs for ultrasound wave reception, each second pMUT having a structure different from that of each first pMUT;
   a substrate on which each of the first pMUTs and second pMUTs are disposed, wherein the substrate includes a thin film part in portions corresponding to the first pMUTs and the substrate does not include the thin film part in portions corresponding to the second pMUTs, wherein the thin film part is thinner than a remainder of the substrate; and
   a cell region of each first pMUT and a cell region of each second pMUT are separated from each other in an ultrasound wave radiation plane,
   wherein each first pMUT has a diaphragm structure and transmits ultrasound waves by a deflection vibration mode and each second pMUT has a non-diaphragm structure and receives ultrasound waves by a thickness vibration mode.

2. The ultrasound probe according to claim 1, wherein:
   each first pMUT has a structure in which a first lower electrode, a first piezoelectric body and a first upper electrode are sequentially stacked on the substrate;
   each second pMUT has a structure in which a second lower electrode, a second piezoelectric body and a second upper electrode are sequentially stacked on the substrate; and
   the first piezoelectric body and the second piezoelectric body are formed of respective materials different from each other.

3. The ultrasound probe according to claim 2, wherein the first piezoelectric body is formed of an inorganic piezoelectric material.

4. The ultrasound probe according to claim 3, wherein the inorganic piezoelectric material is lead zirconate titanate (PZT).

5. The ultrasound probe according to claim 2, wherein the second piezoelectric body is formed of an organic piezoelectric material.

6. The ultrasound probe according to claim 5, wherein the organic piezoelectric material is polyvinylidene fluoride (PVDF) resin.

7. The ultrasound probe according to claim 2, wherein thickness t of the second piezoelectric body is $t \leq V/4F_{max}$, where $F_{max}$ represents a maximum frequency in an ultrasound wave frequency band that is used, and V represents a sound velocity in the second piezoelectric body.

8. The ultrasound probe according to claim 1, wherein:
   the diaphragm structure of each first pMUT exhibits the deflection vibration mode in which a vibration plate of the diaphragm structure is caused to deflect in response to expansion and contraction of the vibration plate in an ultrasound frequency band; and
   the non-diaphragm structure of each second pMUT does not exhibit the deflection vibration mode in the ultrasound frequency band.

9. The ultrasound probe according to claim 1, wherein a center-to-center distance L of cells of one of the first pMUTs and one of the second pMUTs adjacent to each other is $L \leq \lambda_c/2$, where $\lambda_c$ represents a wavelength in a living body with respect to a center frequency Fc of an ultrasound wave frequency band that is used.

10. The ultrasound probe according to claim 1, wherein:
    the plurality of pMUTs are divided into a plurality of channels; and
    a number of the plurality of first pMUTs and a number of the plurality of second pMUTs in each channel are different from each other.

11. The ultrasound probe according to claim 1, wherein the pMUT array includes:
    an electronic circuit substrate configured to drive and control a piezoelectric element of each first pMUT and a piezoelectric element of each second pMUT;
    a piezoelectric element portion including a piezoelectric element substrate on which the piezoelectric elements are each formed; and
    a connector interposed between the electronic circuit substrate and the piezoelectric element substrate,
    wherein the electronic circuit substrate and the piezoelectric element substrate are physically and electrically connected with each other by the connector.

12. The ultrasound probe according to claim 1, wherein:
    the pMUT array includes an electronic circuit substrate configured to drive and control a piezoelectric element of each first pMUT and a piezoelectric element of each second pMUT;
    the piezoelectric elements are formed on the electronic circuit substrate with an insulation layer interposed between the piezoelectric elements and the electronic circuit substrate; and
    the electronic circuit substrate and the piezoelectric element are electrically connected with each other by a through electrode provided in the insulation layer.

13. An ultrasound diagnostic apparatus comprising:
    the ultrasound probe according to claim 1; and
    an ultrasound diagnostic apparatus main body to which the ultrasound probe is connected, the ultrasound diagnostic apparatus main body being configured to generate an ultrasound image based on an ultrasound signal from the ultrasound probe.

14. The ultrasound probe according to claim 1, wherein each first pMUT has a structure in which a first lower electrode, a first piezoelectric body and a first upper electrode are sequentially stacked on the substrate, each second pMUT has a structure in which a second lower electrode, a second piezoelectric body and a second upper electrode are sequentially stacked on the substrate, and wherein the first piezoelectric body of each first pMUT forms the diaphragm structure with the substrate and transmits ultrasound waves by a deflection vibration mode and the second piezoelectric body of each second pMUT forms the non-diaphragm structure with the substrate.

15. The ultrasound probe according to claim 14, wherein the diaphragm structure of the first PMUT exhibits deflection mode resonance with at least one resonance point in an ultrasound frequency band and the diaphragm structure of the second PMUT exhibits no deflection mode resonance in the ultrasound frequency band.

* * * * *